United States Patent [19]

Ohno et al.

[11] Patent Number: 4,882,084
[45] Date of Patent: Nov. 21, 1989

[54] OPTICALLY ACTIVE SUBSTITUTED BIPHENYL COMPOUNDS

[75] Inventors: Kouji Ohno; Shinichi Saito; Kazutoshi Miyazawa, all of Yokohama; Makoto Ushioda, Kawasaki; Hiromichi Inoue; Naoyuki Yoshida, both of Yokohama, all of Japan

[73] Assignee: Chisso Corporation, Osaka, Japan

[21] Appl. No.: 113,763

[22] Filed: Oct. 28, 1987

[30] Foreign Application Priority Data

Nov. 7, 1986 [JP] Japan ................................. 61-263837
Nov. 17, 1986 [JP] Japan ................................. 61-273589

[51] Int. Cl.$^4$ ........................ C09K 19/12; C09K 19/52; G02F 1/13; C07C 67/02
[52] U.S. Cl. ........................... 252/299.66; 252/299.01; 350/350 S; 500/255; 558/414
[58] Field of Search .................... 252/299.66, 299.01; 350/350 S; 558/414; 560/255

[56] References Cited

U.S. PATENT DOCUMENTS 4,556,727 12/1985 Walba .............................. 252/299.01
4,725,688  2/1988 Taguchi et al. ................. 252/299.01

FOREIGN PATENT DOCUMENTS 255219  2/1988 European Pat. Off. ........ 252/299.66
288297 10/1988 European Pat. Off. ............ 560/255
8705012  8/1987 World Int. Prop. O. .
8705018  8/1987 World Int. Prop. O. ...... 252/299.66

Primary Examiner—John F. Terapane
Assistant Examiner—J. E. Thomas
Attorney, Agent, or Firm—Wenderoth, Lind & Ponack

[57] ABSTRACT

The optically active compounds of the formula:

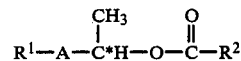

wherein $R^1$ is an alkyl or an alkyloxy group having a carbon number of 1-18, $R^2$ is an alkyl group having a carbon number of 1-18, and A is a biphenyl group or a biphenyl group having a halogen atom or a cyano group are provided.

The optically active compounds are useful for liquid crystal elements, especially for components of ferroelectric liquid crystal mixtures inducing high value of spontaneous polarization.

5 Claims, No Drawings

OPTICALLY ACTIVE SUBSTITUTED BIPHENYL COMPOUNDS

BACKGROUND OF THE INVENTION

The present invention relates to liquid crystal materials for use in liquid crystal display elements, and to substances useful for these components. More particularly, the present invention relates to new chiral materials useful for components of ferroelectric liquid crystal mixtures, and to liquid crystal mixtures containing these materials.

Display element of a twisted nematic (TN) type is widely used as a liquid crystal display element. The liquid crystal display is characterized in less eyestrain and minimized consumption of electric power because it is a non-emissive type. However, the display element of the TN type has an unsolved disadvantage in which the response is slower than that of a display element of light emitting type (e.g. an electroluminescence display, a plasma display and the like). The improvement of the response time of the liquid crystal display is tried in many ways. As a liquid crystal display using a different principle instead of the TN type display, a display method using a ferroelectric liquid crystal is reported by N. A. Clark et al. (ref. Appl. Phys. Lett. 36, 899 (1980)).

This display method utilizes a chiral smectic C phase (abbreviated as $S_C^*$ phase hereinafter) or a chiral smectic H phase (abbreviated as $S_H^*$ phase hereinafter) of ferroelectric liquid crystals, and it has three excellent characteristics in comparison with the TN display method. The first characteristic is quick response and the response time is less than 1/100 of that of the TN display element. The second characteristic is that the method has memory effect and it facilitates multiplexed drive in cooperation with the quick response. The third charateristic is to obtain easily its gray scale. There are problems of temperature dependence of threshold voltage, electric voltage dependence of response speed and the like because applied voltage is controlled for obtaining the gray scale in the TN method. In comparison with the TN method, the display method applying the light switching effect of the $S_C^*$ phase is suitable for graphic display because it is able to obtain the gray scale by controlling inversion time of polarity.

For such materials of ferroelectric liquid crystals having excellent characteristics, liquid crystal compounds having the $S_C^*$ phase and the high value of spontaneous polarization (abbreviated as Ps hereinafter) were desired. Afterward, it was found that a ferroelectric liquid crystal mixture was obtained by adding a chiral and optically active compound, which does not show a liquid crystal phase by itself, to a smectic liquid crystal. Thus, search fields of the materials of ferroelectric liquid crystals were more widened (ref. Mol. Cryst. Liq. Cryst. 89, 327 (1982)).

SUMMARY OF THE INVENTION

Accordingly, an object of the present invention is to provide new optically active materials which are compatible with conventional liquid crystal materials and obtainable mixtures of ferroelectric liquid crystals by solving into smectic liquid crystals. The other object of the present invention is to provide mixtures of smectic liquid crystals having the high value of spontaneous polarization and light switch elements having the high response speed.

The first feature of the present invention is an optically active compound represented by the general formula:

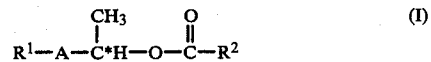

wherein $R^1$ indicates an alkyl or alkyloxy group having a carbon number of 1-18, $R^2$ indicates an alkyl group having a carbon number of 1-18, A indicates

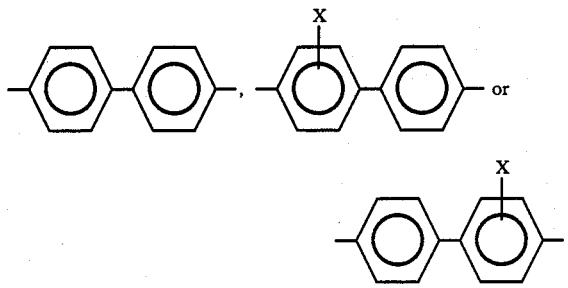

and X indicates a halogen atom or a cyano group.

The second feature of the present invention is a ferroelectric liquid crystal mixture characterized in that the mixture contains at least one smectic liquid crystal material and at least one optically active material represented by the above general formula (I).

The third feature of the present invention is a light switching element for using the above described ferroelectric liquid crystal mixture.

DESCRIPTION OF PREFERRED EMBODIMENTS

Materials provided by the present invention are optically active 4-alkyl-4'-(1-alkanoyloxyethyl)biphenyl and 4-alkyloxy-4'-(1-alkanoyloxyethyl)biphenyl, and the optically active biphenyls in which one of the benzene rings is laterally mono-substituted by a halogen atom or a cyano group. Optically active biphenyl derivatives such as 4-pentyl-4'-(1-hexanoyloxyethyl)biphenyl, 4-pentyl-4'-(1-butanoyloxyethyl)biphenyl, 4-octyloxy-4'-(1-hexanoyloxyethyl)biphenyl, 4-octyloxy-4'-(1butanoyloxyethyl)-biphenyl and the like, and an optically active biphenyl derivative which is substiuted by a fluorine atom at the 3- or 3'-position thereof, etc., can be exemplified.

The optically active biphenyl derivatives which are provided by the present invention are soluble in many known liquid crystal materials. Thus, the derivatives can be mixed as components of the liquid crystal materials. In particular, the derivatives can be preferably used as components of ferroelectric liquid crystal mixtures. As shown in the examples described hereinafter, even though the optically active biphenyl derivative of the present invention shows no liquid crystal phase by itself, it can realize a high Ps value in a smectic liquid crystal mixture when it is used as a component thereof. Such potential spontaneous polarization produces best effects by adding the optically active biphenyl derivative of the present invention to the smectic C liquid crystal.

The smectic C liquid crystal mixture obtained by the above addition of the optically active compound of the present invention induces a spontaneous polarization of several nanocoulombs per square centimeter which is a sufficient practical value for the light switch element of quick response.

The optically active biphenyl derivatives of the present invention are obtained, e.g., by condensation of an optically active 4-substiuted-4'-(1-hydroxyethyl)-biphenyl represented by formula (II) and a fatty acid represented by formula (III),

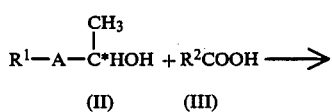

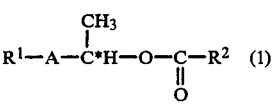

wherein $R^1$, $R^2$ and A show the same meaning as decribed above, respectively.

The optically active alcohol represented by formula (II) is obtained by a biochemical reaction of asymmetric transesterification between a racemic alcohol obtained by the following process of Scheme 1 or Scheme 2 and a triglyceride of a lower fatty acid. Namely, the biochemical transesterification is conducted by any racemic alcohol of a pair of antipodes. Accordingly, an alcohol which has been produced by hydrolyzing the resulting ester, and an alcohol which has not produced an ester in the biochemical reaction, form antipodes of each other.

Scheme 1
(Racemic alcohol wherein $R^1$ is an alkyloxy group)

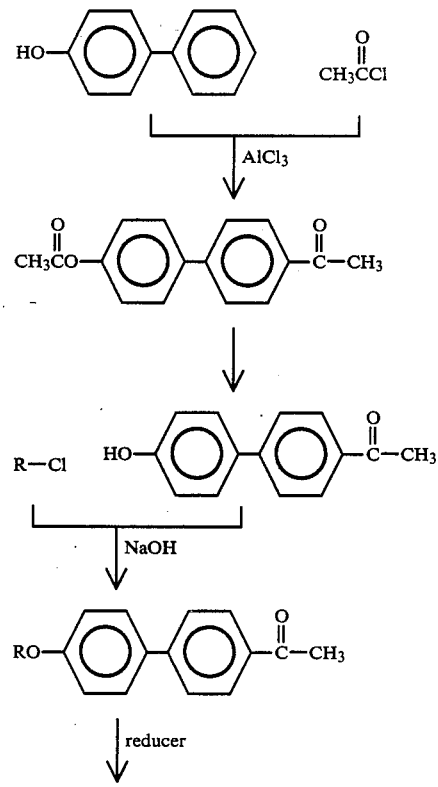

-continued
Scheme 1
(Racemic alcohol wherein $R^1$ is an alkyloxy group)

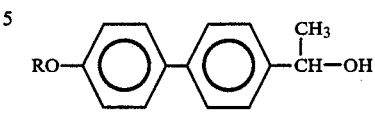

wherein R indicates an alkyl group.

Scheme 2
(Racemic alcohol wherein $R^1$ is an alkyl group)

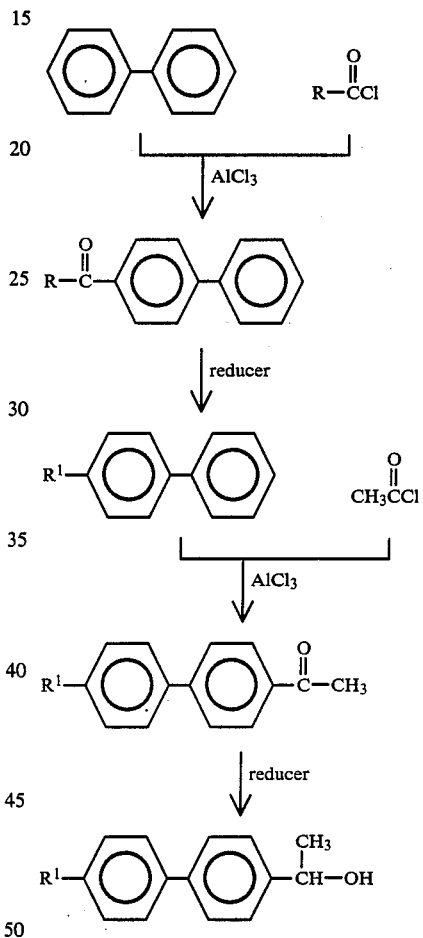

the racemic alcohol which is laterally substituted by a halogen atom or a cyano group at one of the phenylene rings can be prepared by the same synthetic method as described above.

the above biochemical reaction of asymmetric transesterification is conducted in a liquid phase in the substantial absence of water at 30°–45° C. by using an enzyme such as a lipase. The reaction is carried out in about one to thirty days. When a homogeneous phase is unobtainable by the racemic alcohol and the triglyceride alone, a solvent of hydrocarbon such as heptane, hexane, toluene, etc., can be used in the asymmetric transesterification reaction.

One of the antipodes of the optically active esters of the present invention can also be obtained by the above biochemical reaction of transestericication. The other antipode ester can be prepared according to equation (1) wherein the starting material is an alcohol which does not biochemically form an ester.

The ferroelectric liquid crystal mixture provided by the present invention is easily obtained by dissolving the optically active compound represented by formula (I) in the known material of smectic liquid crystals. As the material of smectic liquid crystals, the material which shows a smectic C phase (abbreviated as $S_C$ phase) is preferably used. The liquid crystal compounds represented by the following general formulas can be illustrated as the liquid crystal compounds which show the $S_C$ phase.

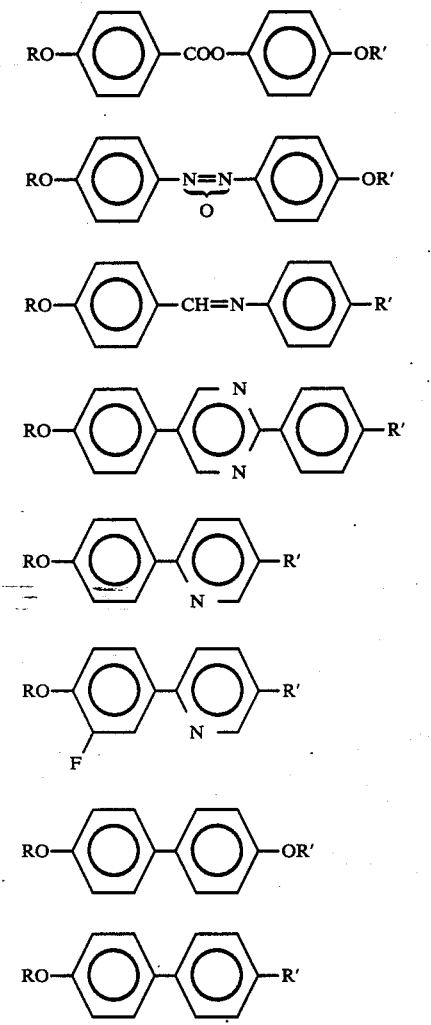

wherein R and R' indicate an alkyl group, respectively.

The quantity of optically active material of formula (I) mixed in these $S_C$ liquid crystals is dependent on kinds of $S_C$ liquid crystals and the mixed ratio, and it is suitably about 1–30 percent by weight. When the content of the chiral compound of formula (I) is less than one percendt by weight, it is difficult to obtain a sufficient Ps value. When the content exceeds 30 percent by weight, the disadvantage becomes remakable that the temperature region of the $S_C^*$ phase of the obtained mixture is limited.

When the optically active compound provided by the present invention is added to an ordinary smectic C liquid crystal, it is suited to use as a component of the ferroelectric liquid crystal mixture because its viscosity is not excessively increased.

It is commonly known that a sign of spontaneous polarization induced in a smectic liquid crystal mixture obtained by adding one of the antipodal optically active compounds is opposite to that induced by adding the other of the antipodes to a smectic mixture. According to the present invention, as the pair of antipodes are easily obtained, the chiral compounds which give the sign of the desired spontaneous polarization in the ferroelectric materials is easily provided.

Furthermore, the chiral smectic C liquid crystal mixtures which are obtained by adding the optically active compounds of the present invention as the components, show a big value of the sponteneous polarization.

Thus, by using the $S_C$ liquid crystal mixtures as the materials, it is possible to obtain liquid crystal elements having quick response.

A small amount of the optically active compounds of the present invention as a chiral dopant can also be used by adding to an ordinary nematic liquid crystal as shown in the reference example described later.

The following examples illustrate the present invention more specifically, but these will not always be precise in practical applications.

EXAMPLE 1

(−)-4-octyloxy-4'-(1-hexanoyloxyethyl)biphenyl

Racemic(±)-4-octyloxy-4'-(1-hydroxyethyl)biphenyl (m.p. 110.9°–111.9° C.) and tributyrin were biochemically transesterified. The obtained 7.0 g (21 mmol) of optically active (−)-4-octyloxy-4'-(1-hydroxyethyl)-biphenyl (m.p. 123.6° C., $[\alpha]_D^{24.5}$ −27.0° (c 1.0, $CHCl_3$)), 7.5 g(36 mmol) of N,N'-dicyclohexylcarbodiimide (abbreviated as DCC) and 1.0 g of 4-dimethylaminopyridine (abbreviated as DMAP) were dissolved in 200 ml of dichloromethane. To the solution, 3.4 g (29 mmol) of caproic acid was added, and the mixture was stirred for six hours at room temperature. The deposited crystals were filtered, 200 ml of water was added to the filtrate, and the organic layer was separated. 6N hydrochloric acid was added to the organic solution, and then the solution was neutralized with the aqueous solution of 2N sodium hydroxide. The neutralized solution was washed with water until the washed water became neutral. The solvent and low-boiling fractions were distilled away from the obtained solution. The residue was recrystallized from ethanol and the desired (−)-4-octyloxy-4'-(1-hexanoyloxyethyl)biphenyl 6.8 g was obtained. The melting point of the obtained biphenyl was 60.8° C. and its specific optical rotation was −78.4° at 25.3° C. for D line (c 0.88, $C_2H_5OH$).

EXAMPLE 2

Optically active 4-pentyl-4'-(1-hexanoyloxyethyl)-biphenyl

Racemic (±)-4-pentyl-4'-(1-hydroxyethyl)biphenyl (m.p. 90.0° C.) was optically resolved by biochemical transesterification. Using the obtained 5.0 g of (−)-4-pentyl-4'-(1-hydroxyethyl)biphenyl (m.p. 83.8° C., $[\alpha]_D^{24.5}$ −25.0° (c 1.0, $CH_3OH$)), 7.0 g of DCC, 1.0 g of DMAP and 3.0 g of caproic acid, optically active 4-pentyl-4'-(1-hexanoyloxyethyl)biphenyl 3.2 g was obtained by the same method as described in Example 1. The melting point of the obtained biphenyl was 10° C.

EXAMPLE 3

The phase transition of liquid crystal mixture (A) containing the following six components:

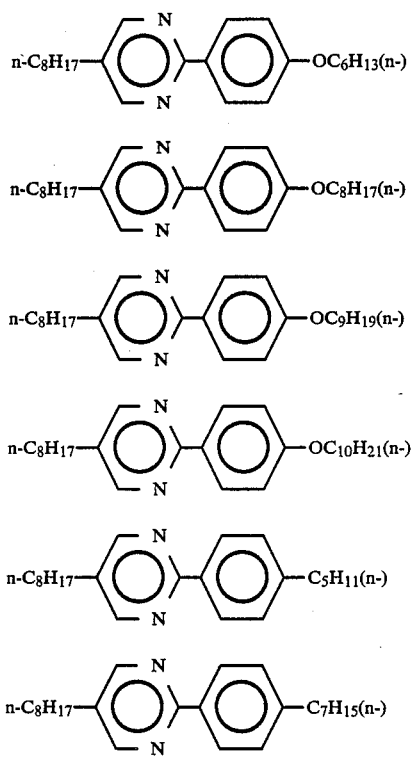

30 wt %

20 wt %

10 wt %

10 wt %

20 wt %

10 wt % was represented by the following:

wherein C, $S_A$, N and I indicate a crystal phase, a smectic A phase, a nematic phase and an isotropic liquid phase, respectively.

To 90 parts by weight of this mixture (A), 10 parts by weight of the optically active compound:

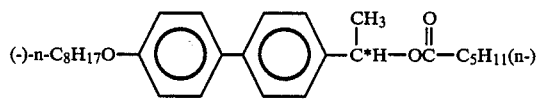

prepared in Example 1 was added, and a mixture of liquid crystals was produced.

This mixture showed the $S_C^*$ phase at temperatures of 2° C.-37° C., the Ps value was 4.4nC/cm² at 25° C., and the tilt angle was 12°.

Furthermore, this mixture was sealed in a cell 2μm in thickness having transparent electrodes obtained by homogeneous aligning treatment. The treatment was conducted by application of polyvinyl alcohol of an aligning agent to the surfaces of the electrodes and rubbing the applied surfaces.

The resulting cell of liquid crystals was placed between two crossed polarizing plates and 10 V of peak value of square waves was applied to the cell. The change of transmittance of light was observed. The response time of this liquid crystal cell that was determined by the intensity change of transmittance light was 100μsec. at 25° C.

REFERENCE EXAMPLE

A mixture of nematic liquid crystals containing the following four components:

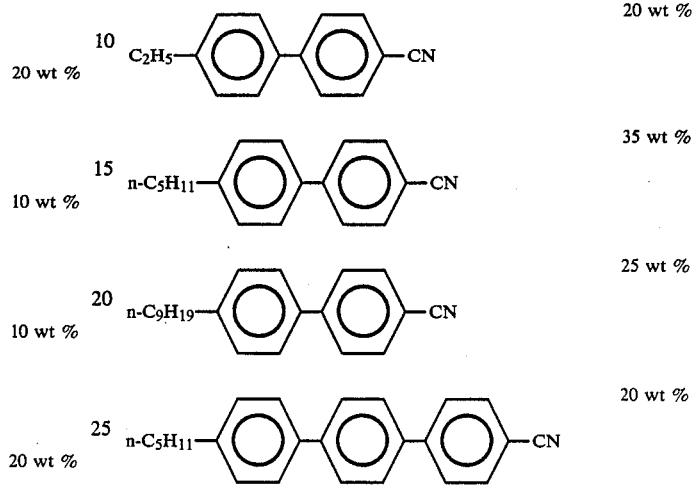

20 wt %

35 wt %

25 wt %

20 wt % was sealed in a cell having transparent electrodes at intervals 10μm which were obtained by homogeneous aligning treatment, for which polyvinylalcohol of the aliging agent was applied to the surfaces of the electrodes and the surfaces were rubbed. The resulting display cell of TN type was observed under a polarization microscope, and it was found that reverse twist demain was produced.

To the mixture of nematic liquid crystals, 0.1 percent by weight of the optically active compound:

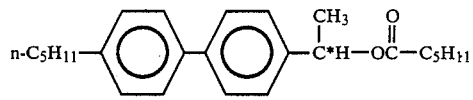

prepared in Example 2 was added. The resulting mixture was sealed in a cell to prepare a cell of TN type. The cell was observed by the same method as described in the above. The reverse twist demain was dissolved, and a homogeneous nematic phase was observed.

We claim:

1. An optically active compound of the formula:

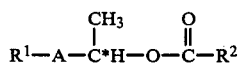

wherein $R^1$ is an alkyl or alkyloxy group having a carbon number of 1-18, $R^2$ is an alkyl group having a carbon number of 1-18, A is

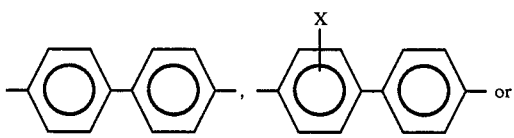

or

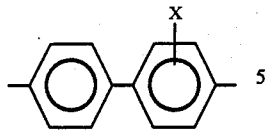

and X is a halogen atom or a cyano group.

2. An optically active compound as claimed in claim 1, wherein $R^1$ is an octyloxy group, $R^2$ is a pentyl group and A is a biphenyl-4, 4'-diyl group.

3. An optically active compound as claimed in claim 1, wherein $R^1$ and $R^2$ is a pentyl group and A is a biphenyl-44'-diyl group.

4. A ferroelectric liquid crystal mixture comprising at least one smectic liquid crystal compound and at least one optically active compound of the general formula:

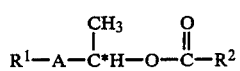

wherein $R^1$ is an alkyl or alkyloxy group having a carbon number of 1-18, $R^2$ is an alkyl group having a carbon number of 1-18, a is

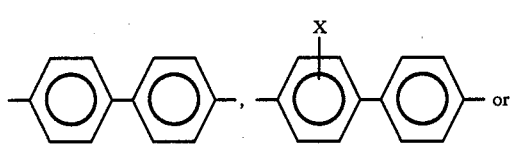

and X is a halogen atom or a cyano group.

5. A light switching element which comprises a ferroelectric liquid crystal mixture comprising at least one smectic liquid crystal compound and at least one optically active compound of the general formula:

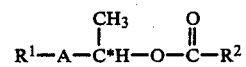

wherein $R^1$ is an alkyl or alkyloxy group having a carbon number of 1-18, $R^2$ is an alkyl group having a carbon number of 1-18, A is

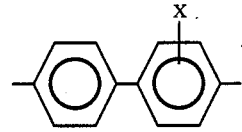

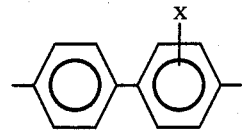

and X is a halogen atom or a cyano group.

* * * * *